(12) United States Patent
Nilsson et al.

(10) Patent No.: US 7,638,623 B2
(45) Date of Patent: Dec. 29, 2009

(54) GALACTOSIDE INHIBITORS OF GALECTINS

(75) Inventors: Ulf Nilsson, Lund (SE); Hakon Leffler, Lund (SE); Ian Cumpstey, Stockholm (SE)

(73) Assignee: Forskarpatent I SYD AB, Lund (SE)

( * ) Notice: Subject to any disclaimer, the term of this patent is extended or adjusted under 35 U.S.C. 154(b) by 0 days.

(21) Appl. No.: 11/561,124

(22) Filed: Nov. 17, 2006

(65) Prior Publication Data

US 2007/0185039 A1    Aug. 9, 2007

Related U.S. Application Data

(63) Continuation of application No. PCT/SE2005/000757, filed on May 20, 2005.

(30) Foreign Application Priority Data

May 21, 2004    (SE)    ................... 0401300

(51) Int. Cl.
   *C13K 13/00*    (2006.01)
   *A61K 31/7016*  (2006.01)
(52) U.S. Cl. .................... 536/123.13; 514/53
(58) Field of Classification Search ............ 536/123.13; 514/53
   See application file for complete search history.

(56) References Cited

U.S. PATENT DOCUMENTS 7,186,681 B2 * 3/2007 Liu et al. ................. 514/2

2002/0044932 A1 * 4/2002 Liu et al. ................. 424/143.1
2006/0148712 A1 * 7/2006 Liu et al. ................. 514/13

FOREIGN PATENT DOCUMENTS

| EP | 0561523 | 9/1993 |
|---|---|---|
| WO | 0007624 | 2/2000 |
| WO | 02057284 A1 | 7/2002 |

OTHER PUBLICATIONS

Leffler et al. Journal of Biological Chemistry, 1986, 261(22), p. 10119-10126.*
Hough et al. J. Chem. Soc. Perkin I, 1973, p. 784-788.*
Helland et al., "Methyl 3-amino-3deoxy-B-D-galactopyranosyl-(1-4)-2-acetamido-20deoxy-B-D-glucopyranoside: an inhibitor of UDP-D-galactose: B-D-galactopyranosyl-(1-4)-2 acetamido-2-deoxy-D-glucose (1-3) a-D-galactopyranosyltransferase" Carbohydrate Research 276 (1995) pp. 91-98.
Schwartz et al., "Thermodynamics of bovine Spleen Galectin-1 Binding to Disacchrides: Correlation with Structure and Its Effect on Oligomerization at the Denaturation Temperature" Biochemistry, 1998, 37, pp. 5867-5877.
Bachhawat-Sikder et al., "Thermodynamic analysis of the binding of galactose and poly-N-acetyllactosamine derivatives to human galectin-3" Federation of European Biochemical Societies Letters, 500 (2001), pp. 75-79.

(Continued)

*Primary Examiner*—Shaojia Anna Jiang
*Assistant Examiner*—Jonathan S Lau
(74) *Attorney, Agent, or Firm*—Gauthier & Connors LLP

(57) ABSTRACT

The present invention relates to novel compounds and the use of said compounds as a medicament, as well as for the manufacture of a medicament for treatment of disorders relating to the binding of galectin to receptors in a mammal. Said galectin is preferably galectin-3.

15 Claims, 4 Drawing Sheets

OTHER PUBLICATIONS

Oberg et al., "Efficient and Expedient Two-Step Pyranose-Retaining Fluorescein Conjugation of Complex Reducing Oligosaccharides: Galectin Oligosaccharide Specificity Studies in Fluorescence Polarization" Bioconjugate Chem. 2003, 14, 2003 American Chemical Society, pp. 1289-1297.

Sorme et al., "Low Micromoler Inhibitors of Galectin-3 Based on 3'-Derivatization of N-Acetyllactosamine" ChemBioChem, 2002, 3, pp. 183-189.

* cited by examiner

A——B-Gal--D-E

GALACTOSIDE INHIBITORS OF GALECTINS

PRIORITY INFORMATION

This application is a continuation of International Application Serial No. PCT/SE2005/000757 filed on May 20, 2005 which claims priority to Swedish Application No. 0401300-9 filed May 21, 2004, both of which are incorporated herein by reference in their entireties.

TECHNICAL FIELD OF THE INVENTION

The present invention relates to novel compounds, the use of said compounds as medicament and for the manufacture of a medicament for the treatment of any disorder relating to the binding of a galectin receptor in mammals. The invention also relates to pharmaceutical compositions comprising said novel compounds.

BACKGROUND ART

Galectins are proteins with a characteristic carbohydrate recognition domain (CRD) (Barondes et al., 1994; Leffler et al., 2004) (FIG. 1a). This is a tightly folded β-sandwich of about 130 aa (about 15 kDa) with the two defining features 1) a β-galactose binding site (C in FIG. 1a) and 2) sufficient similarity in a sequence motif of about seven amino acids, most of which (about six residues) make up the β-galactose binding site. However, adjacent sites (A, B, D, E in FIG. 1a) are required for tight binding of natural saccharides and different preferences of these give galectins different fine specificity for natural saccharides.

The recent completion of the human, mouse and rat genome sequences reveal about 15 galectins and galectin-like proteins in one mammalian genome with slight variation between species (Leffler et al., 2004; Houzelstein et al., 2004).

Galectin subunits can contain either one or two CRDs within a single peptide chain. The first category, mono-CRDs galectins, can occur as monomers or dimers (two types) in vertebrates. The by far best studied galectins are the dimeric galectin-1, and galectin-3 that is a monomer in solution but may aggregate and become multimeric upon encounter with ligands (Leffler et al., 2004; Ahmad et al., 2004). These were the first discovered galectins and are abundant in many tissues. However, our recent phylogenetic analysis (FIG. 2) suggest that galectins with two CRDs within a peptide chain, bi-CRD galectins, appear to be more ancient and more central to the family than previously thought and that most of mammalian mono-CRD galectins may have descended from one or the other CRD of a bi-CRD galectin.

There are now over 1200 publications on galectins in PubMed, with most, as mentioned above, about galectins-1 and -3. Strong evidence suggests roles for galectins in e.g. inflammation, cancer, and development recently reviewed in a special issue (Leffler (editor), 2004b) but a unifying model of the "basic function" of galectins at the cellular-molecular level is lacking.

Galectins are synthesized as cytosolic proteins, without a signal peptide on free ribosomes. Their N-terminus is acetylated, a typical modification of cytosolic proteins, and they reside in the cytosol for a long time (not typical of secreted proteins). From there they can be targeted to the nucleus, specific cytososlic sites, or secreted (induced or constitutively) by a non-classical (non-ER-Golgi) pathway, as yet unknown, but possibly similar to the export of e.g. IL-1 (Leffler et al., 2004). They can also function in all these compartments; for galectin-3, solid evidence published in well respected journals support roles in RNA splicing in the nucleus, inhibition of apoptosis in the cytosol, and a variety of extracellular effects on cell signaling and adhesion (Patterson et al., Ochieng et al., Takenaka et al., Hsu et al. and others in Leffler (editor), 2004b). Gallectin-7 and -12 also act in the cytosol by enhancing apoptosis and regulating the cell cycle and differentiation in certain cells (Hsu and Liu in Leffler (editor), 2004b). Most galectins act also extracellularly by cross-linking glycoproteins (e.g. laminin, integrins, and IgE receptors) possibly forming supramolecular ordered arrays (Brewer et al., 2002) and may thereby modulate cell adhesion and induce intracellular signals.

The present invention relates mainly to galectin-3, but its principles may be applicable also to other galectins.

Potential therapeutic use of galectin-3 inhibitors. Galectin-3 has been implicated in diverse phenomena and, hence, inhibitors may have multiple uses. It is easy to perceive this as a lack of specificity or lack of scientific focus. Therefore, the analogy with aspirin and the cyclooxygenases (COX-I and II) is useful. The COXs produce the precursor of a wide variety of prostaglandins and, hence, are involved in a diverse array of biological mechanisms. Their inhibitors, aspirin and other NSAIDs (non-steroid anti-inflammatory drugs), also have broad and diverse effects. Despite this, these inhibitors are very useful medically, and they have several different specific utilities.

So if galectins, like COXs, are part of some basic biological regulatory mechanism (as yet unknown), they are likely to be 'used by nature' for different purpose in different contexts. Galectin inhibitors, like NSAIDs, are not expected to wipe out the whole system, but to tilt the balance a bit.

Inhibition of Inflammation.

A pro-inflammatory role of galectin-3 is indicated by its induction in cells at inflammatory sites, a variety of effects on immune cells (e.g. oxidative burst in neutrophils, chemotaxis in monocytes), and decrease of the inflammatory response, mainly in neutrophils and macrophages, in null mutant mice (chapters by Rabinovich et al., Sato et al., and Almkvist et al. in Leffler (editor), 2004b). Moreover, knock-out mice of Mac-2BP, a galectin-3 ligand, have increased inflammatory responses (Trahey et al., 1999). Inflammation is a protective response of the body to invading organisms and tissue injury. However, if unbalanced, frequently it is also destructive and occurs as part of the pathology in many diseases. Because of this, there is great medical interest in pharmacological modulation of inflammation. A galectin-3 inhibitor is expected to provide an important addition to the arsenal available for this.

Treatment of Septic Shock.

The idea of a possible role of galectin-3 in septic shock comes from our own studies (Almquist et al., 2001). Briefly, the argument goes as follows. It is known that septic shock involves dissemination of bacterial lipopolysaccharide into the blood stream, and that the pathological effects of this are mediated via neutrophil leukocytes (Karima et al., 1999). LPS does not activate the tissue-damaging response of the neutrophil. Instead, it primes the neutrophil, so that it is converted from unresponsive to responsive to other, presumably endogenous, activators. In septic shock, this priming happens prematurely in the blood stream. Endogenous activators could then induce the tissue damaging response in the wrong place and time. Several candidates have been proposed as these endogenous activators, including TNF-alfa. Inhibitors of these have been used in treatment schemes without much success (Karima et al., 1999). Since our own studies indicate that galectin-3 is a good candidate for being an endogenous activator of primed neutrophils (Almquist et al., 2001), galectin-3 inhibitors may be very useful in septic shock.

Treatment of Cancer.

A large number of immunohistochemical studies show changed expression of certain galectins in cancer (van den Brule et. al. and Bidon et al. in Leffler (editor), 2004b) Galectin-3 is now an established histochemical marker of thyroid cancer, and neoexpression of galectin-4 is a promising marker of early breast cancer (Huflejt and Leffler, 2004). The direct evidence for a role of. galectin-3 in cancer comes from mouse models, mainly by Raz et al, but also others (Takenaka et al. in Leffler (editor), 2004b). In paired tumor cell lines (with decreased or increased expression of galectin-3), the induction of galectin-3 gives more tumors and metastasis and suppression of galectin-3 gives less tumors and metastasis. Galectin-3 has been proposed to enhance tumor growth by being anti-apoptotic, promote angiogenesis, or to promote metastasis by affecting cell adhesion. From the above it is clear that inhibitors of galectin-3 might have valuable anti-cancer effects. Indeed, saccharides claimed but not proven to inhibit galectin-3 have been reported to have anti-cancer effects. In our own study a fragment of galectin-3 containing the CRD inhibited breast cancer in a mouse model by acting as a dominant negative inhibitor (John et al., 2003).

Also galectin-1 is frequently over-expressed in low differentiated cancer cells, and galectin-9 or its relatives galectin-4 and galectin-8 may be induced in specific cancer types (Huflejt and Leffler, 2004; Leffler (editor), 2004b). Galectin-1 induces apoptosis in activated T-cells and has a remarkable immunosuppressive effect on autoimmune disease in vivo (Rabinovich et al; and Pace et al. in Leffler (editor), 2004b. Therefore, the over-expression of these galectins in cancers might help the tumor to defend itself against the T-cell response raised by the host (Rubinstein et al., 2004). Null mutant mice for galectins-1 and -3 have been established many years ago (Poirier, 2002). These are healthy and reproduce apparently normally in animal house conditions. However recent studies have revealed subtle phenotypes in function of neutrophils and macrophages (as described above) and in bone formation for galectin-3 null mutants, and in nerve and muscle cell regeneration/differentiation for the galectin-1 null mutants (Leffler et al., 2004; Poirier, 2002; Watt in Leffler (editor), 2004b). Recently galectin-7 and galectin-9 null mutant mice have been generated and are also grossly healthy in animal house conditions, but have not yet been analysed in detail. The differences in site of expression, specificity and other properties make it unlikely that different galectins can replace each other functionally. The observations in the null mutant mice would indicate that galectins are not essential for basic life supporting functions as can be observed in normal animal house conditions. Instead they may be optimizers of normal function and/or essential in stress conditions not found in animal house conditions. The lack of strong effect in null mutant mice may make galectin inhibitors more favorable as drugs. If galectin activity contributes to pathological conditions as suggested above but less to normal conditions, then inhibition of them will have less unwanted side effects.

Known Inhibitors

Natural Ligands.

Solid phase binding assays and inhibition assays have identified a number of saccharides and glycoconjugates with the ability to bind galectins (reviewed by Leffler, 2001 and Leffler et al., 2004). All galectins bind lactose with a $K_d$ of 0.5-1 mM. The affinity of D-galactose is 50-100 times lower. N-Acetyl-lactosamine and related disaccharides bind about as well as lactose, but for certain galectins, they can bind either worse or up to 10 times better. The best small saccharide ligands for galectin-3 were those carrying blood group A-determinants attached to lactose or lacNAc-residues and were found to bind up to about 50 times better than lactose. Galectin-1 shows no preference for these saccharides.

Larger saccharides of the polylactosamine type have been proposed as preferred ligands for galectins. In solution, using polylactosamine-carrying glycopeptides, there was evidence for this for galectin-3, but not galectin-1 (Leffler and Barondes, 1986). A modified plant pectin polysaccharide has been reported to bind galectin-3 (Pienta et al., 1995).

The above-described natural saccharides that have been identified as galectin-3 ligands are not suitable for use as active components in pharmaceutical compositions, because they are susceptible to acidic hydrolysis in the stomach and to enzymatic degradation. In addition, natural saccharides are hydrophilic in nature, and are not readily absorbed from the gastrointestinal tract following oral administration.

Synthetic Inhibitors.

Saccharides coupled to amino acids with anti-cancer activity were first identified as natural compounds in serum, but subsequently, synthetic analogues have been made (Glinsky et al., 1996). Among them, those with lactose or Gal coupled to the amino acid inhibit galectins, but only with about the same potency as the corresponding underivatized sugar. A chemically modified form of citrus pectin (Platt and Raz, 1992) that inhibits galectin-3 shows anti-tumor activity in vivo (Pienta et al., 1995; Nangia-Makker et al., 2002).

A divalent form of a lactosyl-amino acid had higher potency in a solid phase assay (Naidenko et al., 2000; Huflejt et al., 2001; Huflejt and Leffler, 2004) and clusters having up to four lactose moieties showed a strong multivalency effect when binding to galectin-3, but not to galectin-1 and -5 (Vrasidas et al., 2003). Cyclodextrin-based glycoclusters with seven galactose, lactose, or N-acetyllactosamine residues also showed a strong multivalency effect against galectin-3, but less so against galectins-1 and -7 (André et al., 2004). Starburst dendrimers (André et al., 1999) and glycopolymers (Pohl et al., 1999; David et al., 2004), made polyvalent in lactose-residues, have been described as galectin-3 inhibitors with marginally improved potency as compared to lactose. The aforementioned synthetic compounds that have been identified as galectin-3 ligands are not suitable for use as active components in pharmaceutical compositions, because they are hydrophilic in nature and are not readily absorbed from the gastrointestinal tract following oral administration.

Natural oligosaccharides, glycoclusters, glycodendrimers, and glycopolymers described above are too polar and too large to be absorbed and in some cases are large enough to produce immune responses in patients. Furthermore, they are susceptible to acidic hydrolysis in the stomach and to enzymatic hydrolysis. Thus, there is a need for small synthetic molecules Thiodigalactoside is known to be a synthetic and hydrolytically stable, yet polar inhibitor, approximately as efficient as N-acetyllactosamine (Leffler and Barondes, 1986). A library of pentapeptides provided inhibitors against galectin-1 and -3, but only with low affinities, similar to that of galactose (Arnusch et al., 2004). Furthermore, peptides are not ideal agents for targeting galectins in vivo, as they are susceptible to hydrolysis and are typically polar. N-Acetyllactosamine derivatives carrying aromatic amides or substituted benzyl ethers at C-3' have been demonstrated to be highly efficient inhibitors of galectin-3, with unprecedented $IC_{50}$ values as low as 4.8 µM, which is a 20-fold improvement in comparison with the natural N-acetyllactosamine disaccharide (Sörme et al., 2002; Sörme et al., 2003b). These derivatives are less polar overall, due to the presence of the aromatic amido moieties and are thus more suitable as agents for the inhibition of galectins in vivo. However, said 3'-amido-derivatised compounds are still susceptible to hydrolytic degradation in vivo, due to the presence of a glycosidic bond in the N-acetyllactosamine disaccharide moiety and, although they are the best reported small molecule inhibitors of galectin-3, even further improved affinity is desirable.

Thus, there is still a considerable need within the art of inhibitors against galectins, in particular of galectin-3.

SUMMARY OF THE INVENTION

Therefore, the present invention relates to compounds that have the general formula (I):

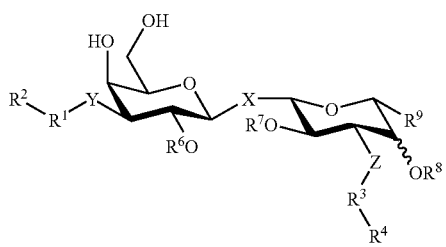

(I)

wherein
the configuration of one of the pyranose rings is β-D-galacto;
X is selected from the group consisting of O, S, SO, $SO_2$, $NH$, $CH_2$, and $NR^5$,
Y is selected from the group consisting of O, S, NH, $CH_2$, and $NR^5$, or is a bond;
Z is selected from the group consisting of O, S, NH, $CH_2$, and $NR^5$, or is a bond;
$R^1$ and $R^3$ are independently selected from the group consisting of CO, $SO_2$, SO, $PO_2$, PO, and $CH_2$ or is a bond;
$R^2$ and $R^4$ are independently selected from the group consisting of;
a) an alkyl group of at least 4 carbons, an alkenyl group of at least 4 carbons, an alkyl group of at least 4 carbons substituted with a carboxy group, an alkenyl group of at least 4 carbons substituted with a carboxy group, an alkyl group of at least 4 carbons substituted with an amino group, an alkenyl group of at least 4 carbons substituted with an amino group, an alkyl group of at least 4 carbons substituted with both an amino and a carboxy group, an alkenyl group of at least 4 carbons substituted with both an amino and a carboxy group, and an alkyl group substituted with one or more halogens; or
b) a heteroaryl group, a phenyl group substituted with at least one carboxy group, a phenyl group substituted with at least one halogen, a phenyl group substituted with at least one alkoxy group, a phenyl group substituted with at least one nitro group, a phenyl group substituted with at least one sulfo group, a phenyl group substituted with at least one amino group, a phenyl group substituted with at least one alkylamino group, a phenyl group substituted with at least one dialkylamino group, a phenyl group substituted with at least one hydroxy group, a phenyl group substituted with at least one carbonyl group and a phenyl group substituted with at least one substituted carbonyl group.
c) a naphthyl group, a naphthyl group substituted with at least one carboxy group, a naphthyl group substituted with at least one halogen, a naphthyl group substituted with at least one alkoxy group, a naphthyl group substituted with at least one nitro group, a naphthyl group substituted with at least one sulfo group, a naphthyl group substituted with at least one amino group, a naphthyl group substituted with at least one alkylamino group, a naphthyl group substituted with at least one dialkylamino group, a naphthyl group substituted with at least one hydroxy group, a naphthyl group substituted with at least one carbonyl group and a naphthyl group substituted with at least one substituted carbonyl group.
d) a heteroaryl group, a heteroaryl group substituted with at least one carboxy group, a heteroaryl group substituted with at least one halogen, a heteroaryl group substituted with at least one alkoxy group, a heteroaryl group substituted with at least one nitro group, a heteroaryl group substituted with at least one sulfo group, a heteroaryl group substituted with at least one amino group, a heteroaryl group substituted with at least one alkylamino group, a heteroaryl group substituted with at least one dialkylamino group, a heteroaryl group substituted with at least one hydroxy group, a heteroaryl group substituted with at least one carbonyl group and a heteroaryl group substituted with at least one substituted carbonyl group.

$R^5$ is selected from the group consisting of hydrogen, an alkyl group, an alkenyl group, an aryl group, a heteroaryl group, and a heterocycle.
$R^6$ and $R^8$ are independently selected from the group consisting of a hydrogen, an acyl group, an alkyl group, a benzyl group, and a saccharide.
$R^7$ is selected from the group consisting of a hydrogen, an acyl group, an alkyl group, and a benzyl group.
$R^9$ is selected from the group consisting of a hydrogen, a methyl group. hydroxymethyl group, an acyloxymethyl group, an alkoxymethyl group, and a benzyloxymethyl group.

The present invention also relates to a compound according to the above-mentioned formula for use as a medicament.

Still further, the present invention relates to the use of a compound according to the above-mentioned formula for the manufacture of a medicament for the treatment of any disorder relating to the binding of a galectin to ligands in a mammal.

Yet further, the present invention relates to a pharmaceutical composition comprising a compound according to the above-mentioned formula as active ingredient together with a pharmaceutically acceptable adjuvant, diluent, excepient or carrier.

Yet further, the present invention relates to a method for inhibiting conditions associated with the binding of galectin to ligands in a mammal, which method comprises administering to said mammal an effective amount of a compound according to the above-mentioned formula.

Still further, the present invention relates to a method for inhibiting conditions associated with the binding of galectin to ligands in a mammal, which method comprises administering. to said mammal an effective amount of a pharmaceutical composition mentioned above.

Galectin Specificity

The studies of galectin specificity using inhibition by small natural saccharides mentioned above indicated that all galectins bound lactose, LacNAc and related disaccharides, but that galectin-3 bound certain longer saccharides much better (Leffler and Barondes, 1986). These longer saccharides were characterized by having an additional sugar residue added to the C-3 position of Gal in lactose or LacNAc. The X-ray crystal structures of galectins-1, -2, and -3 demonstrated a highly conserved core binding site for lactose and LacNAc with features in agreement with the specificity studies (Lobsanov and Rini, 1997; Seetharaman et al., 1998). In addition, an extended groove was found, which might accommodate the added sugar residue in the longer saccharides (A-B in FIG. 1). The shape of this groove varies between galectins, suggesting that the same extensions would not be bound equally by the different galectins. Moreover, including additional galectins (e.g. galectins-4, -8 and -9) it has become clear that there is also variations in binding preference on the other side of the Gal residue (sites D-E in FIG. 1) (Leffler et al., 2004).

Structure-Based Design of Substituted Thiodigalactosides as Galectin Inhibitors.

The extended binding site close to HO-3' of N-acetyllactosamine (site B, FIG. 1b) has been exploited in the design of potent galectin-3-inhibiting 3'-amido-N-actyllactosamine derivatives. (Sörme et al., 2002) In particular, aromatic amides made efficient inhibitors by forming an energetically favorable stacking interaction with the arginine-144 guanidino group of galectin-3. The presence of additional arginine residues in or close to the N-acetyllactosamine binding site of galectin-3 suggests the design of inhibitors that make use of additional stacking interactions between aromatic groups and arginine guanidino groups to provide even more potent inhibitors. The N-acetyl group of N-acetyllactosamine is, according the crystal structure of galectin-3 in complex with N-acetyllactosamine, interacting with arginine-186 of galectin-3 (FIG. 1b). Replacing said N-acetyl group with an aromatic amido group would allow for a new stacking interaction between the aromatic amide and the arginine 186 guanidino group.

Furthermore, replacing the N-acetyllactosamine disaccharide with a hydrolytically stable mimic would add value to an inhibitor in terms of longer half-life in vivo. Thiodigalactoside is such a hydrolytically stable N-acetyllactosamine mimic, which is believed to bind to galectins in a manner mimicking that of N-acetyllactosamine (FIGS. 3A-B). In addition, the synthesis of the symmetrical thiodigalactoside is more economical in comparison with the synthesis of N-acetyllactosamine. As N-acetyllactosamine derivatives carrying aromatic amido groups at C-3' show high affinity for galectin-3 due to an interaction with arginine 144 (FIG. 3C), symmetrical Thiodigalactoside derivatives carrying aromatic amides at the C-3 carbons could be expected to allow the formation of an arene-guanidino interaction between one of the aromatic amido groups and arginine 144 (analogous to the interaction with the 3'-amido-N-acetyllactosamine derivative, FIG. 3D). However, the second aromatic amido-group can be expected to be positioned similarly to the N-acetyl group of N-acetyllactosamine, i.e. close to arginine 186, upon binding to galectin-3; that would be in site D as shown in FIG. 1a). Thus, symmetrical thiodigalactoside derivatives with aromatic amides at both C-3 carbons have the possibility of forming two affinity-enhancing arene-guanidino interactions (FIG. 3D).

Figure 1:
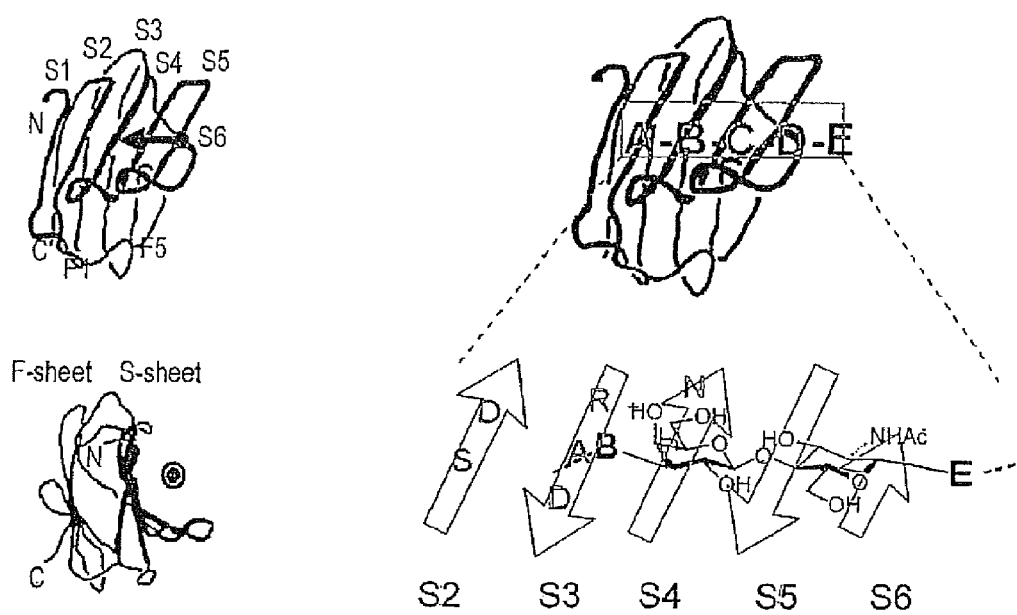
FIG. 1. a) Schematic of the galectin carbohydrate recognition domain (CRD) (left) and carbohydrate binding sites (right) (Barondes et al., 1994; Leffler et al., 2004). The CRD is shown in face and side view with bound disaccharide symbolized by arrow or dot (left). It consists of two β-sheets named S and F. The concave side of the S-sheets forms a groove that can hold about a tetrasaccharide and has four subsites (A-D) with the defining galactose binding site as C, and a fifth subsite (E) outside the groove (top right). A bound LacNAc is shown on the S-beta sheet (bottom right) with extensions into subsite B and E. Pertinent amino acids in galectin-3 around subsite B are indicated in one letter code (grey). b) Structure of carbohydrate recognition site of galectin-3 CRD (smooth surface) with bound LacNAc (stick model). The subsites described in FIG. 1a are indicated below figure with Gal in site C. The arrows indicate spaces in site B targeted by derivatization on position 3 of the Gal (Sörme et al., 2002). Selected amino acids are named. The GlcNAc of the LacNAc is in site D.
Figure 1B:
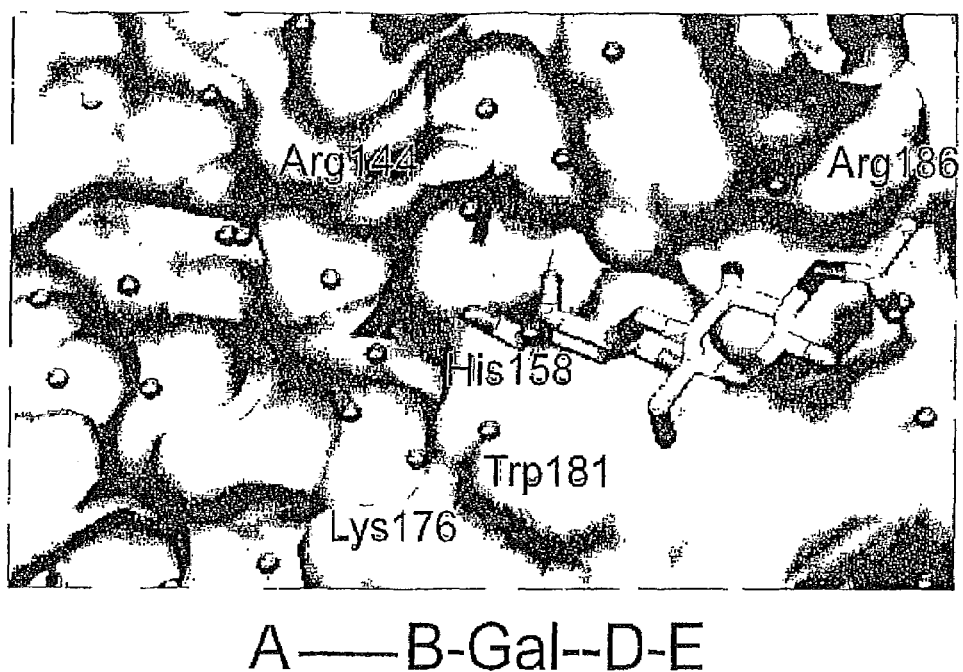
Figure 2:
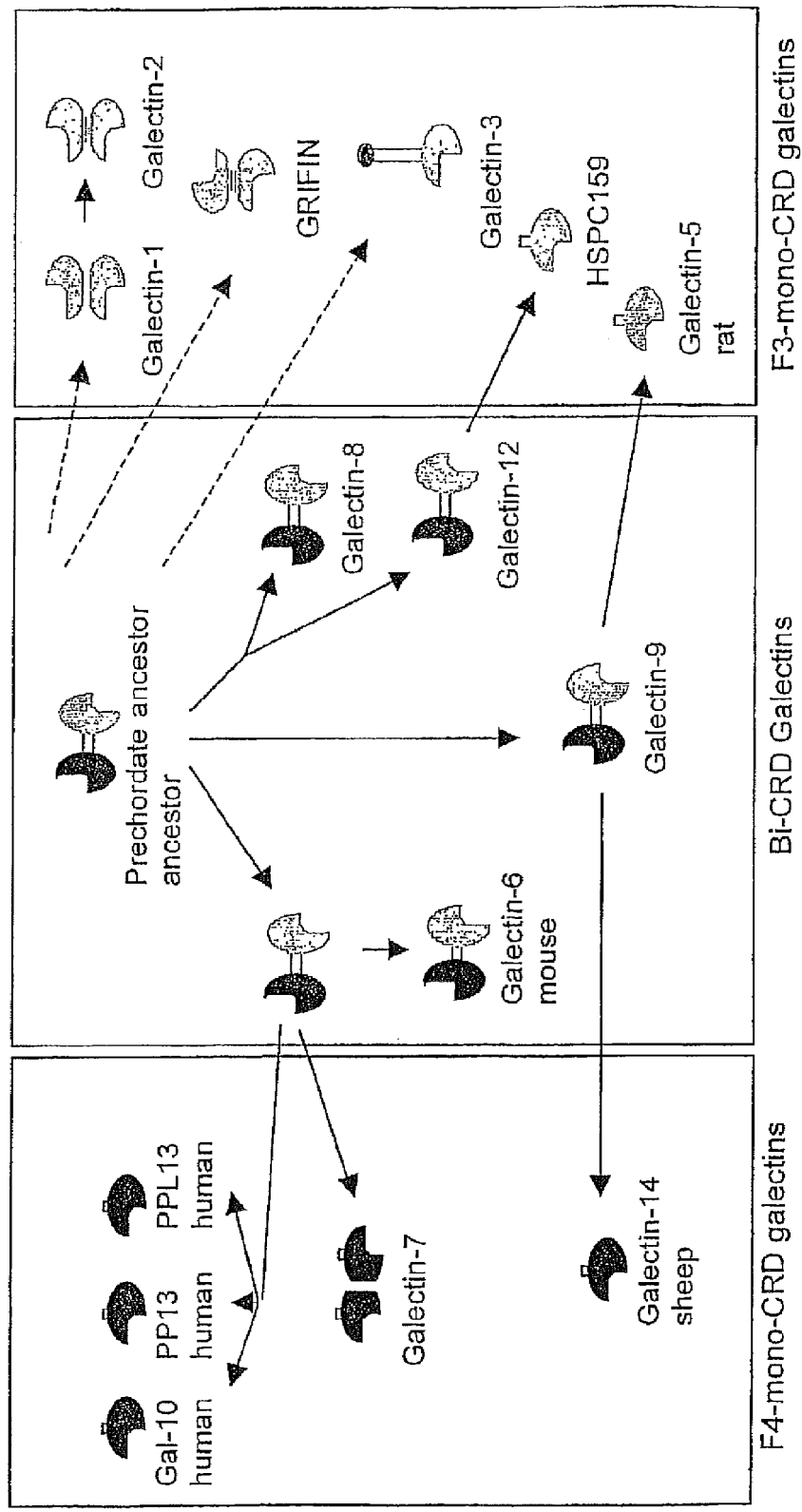
FIG. 2. Mammalian galectins and their phylogeny from a prechordate ancestor (Houzelstein et al., 2004). All the CRDs are of either of two types (F4 and F3, black and grey respectively) defined by corresponding gene structure (intron-exon boundaries) and supported by their respective sequence relationships. The ancestral prechordate galectins include a bi-CRD galectin with one of each CRD type (most likely derived in much earlier evolution from duplication of a mono-CRD galectin). Large scale duplication of genome fragments in early chordate-vertebrate evolution give rise to the four major bi-CRD galectins found in mammals. Local duplication-deletion events give rise to mono-CRD galectins related to either the or C-terminal CRD. Some of these occurred at early more uncertain times (dotted arrows) whereas other are recent and more certain (filled arrows). Recent duplications have also produced extra copies of bi-CRD galectins in certain mammals (e.g. two extra copies of galectin-9s in humans (not shown); galectin-6 in mouse).
Figure 3:
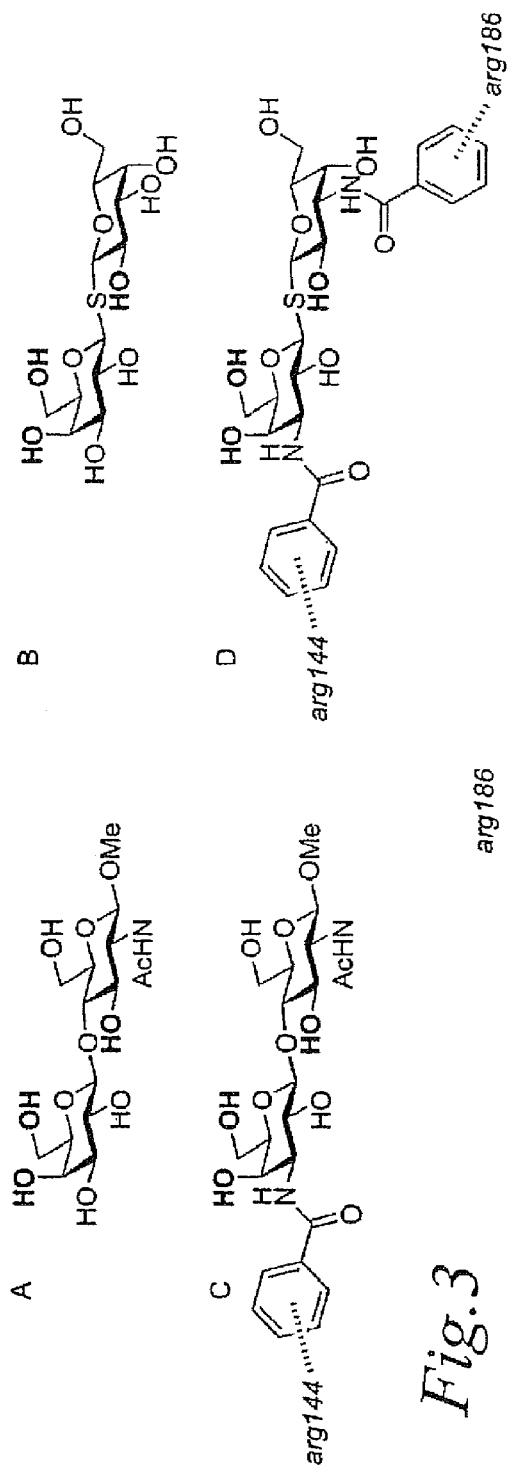
FIG. 3. A) The methyl β-glycoside of N-acetyllactosamine 22. Hydroxyl groups critical for interaction with galectin-3 are in bold face letters. B) Thiodigalactoside 23. Hydroxyl groups critical for interaction with galectin-3 are in bold face letters. C) The 3'-benzamido derivative of the methyl β-glycoside of N-acetyllactosamine. The interaction between the aromatic ring and arginine 144 is depicted with a dashed line. D) The 3,3'-bis-benzamido derivative of thiodigalactoside. The expected interactions between the aromatic rings and arginines 144 and 186 are depicted with dashed lines.

DETAILED DESCRIPTION OF THE PREFERRED
EMBODIMENTS OF THE INVENTION

According to one aspect of the invention, in the above-mentioned formula, X is S and Y and Z are NH.

In the present disclosure, the term "alkyl group" is meant to comprise from 1 to 12 carbon atoms. Said alkyl group may be straight- or branched-chain. Said alkyl group may also form a cycle comprising from 3 to 12 carbon atoms.

In the present disclosure, the term "alkenyl group" is meant to comprise from 2 to 12 carbon atoms. Said alkenyl group comprises at least one double bond.

In the present disclosure the term "aryl group" is meant to comprise from 4 to 18 carbon atoms. Said aryl group may be a phenyl group or a naphthyl group.

In the present disclosure, the term "alkoxy group" is meant to comprise from 1 to 12 carbon atoms. Said alkoxy group may be a methoxy group or an ethoxy group.

In the present disclosure, the term "alkylamino group" is meant to comprise from 1 to 12 carbon atoms.

In the present disclosure, the term "arylamino group" is meant to comprise from 4 to 12 carbon atoms. Said "arylamino group" may be aniline, carboxylated aniline or halogenated aniline.

In the present disclosure, the term "heteroaryl group" is meant to comprise from 4 to 18 carbon atoms, wherein at least one atom of the ring is a heteroatom, i.e. not a carbon. Preferably, said heteroatom is N, O or S. Said heteroaryl group may be a quinoline, isoquinoline pyridine, a pyrrole, a furan or a thiophene group.

In the present disclosure, the term "acyl group" is meant to be aliphatic or aromatic to comprise from 2 to 7 carbon atoms. Said acyl group may be a benzoyl, acetyl, naphthoyl, or a trimethylacetyl group.

In the present disclosure, the term "acyloxy group" is meant to be aliphatic or aromatic and to comprise from 2 to 7 carbon atoms. Said acyloxy group may be a benzoyloxy, acetoxy, naphthoyloxy, or a trimethylacetoxy group.

The above-mentioned groups may naturally be substituted with any other known substituents within the art of organic chemistry. The groups may also be substituted with two or more of the substituents. Examples of substituents are halogen, alkoxy, nitro, sulfo, amino, hydroxy, and carbonyl groups.

In yet another aspect of the invention, said compound is
bis-(3-deoxy-3-benzamido-β-D-galactopyranosyl) sulfane (17),
bis-(3-deoxy-3-(3-methoxybenzamido)-β-D-galactopyranosyl) sulfane (18),
bis-(3-deoxy-(3,5-dimethoxybenzamido)-β-D-galactopyranosyl) sulfane (19),
bis-(3-deoxy-3-(4-nitrobenzamido)-β-D-galactopyranosyl) sulfane (20),
bis(3-deoxy-3-(2-naphthamido)-β-D-galactopyranosyl) sulfane (21),
bis-(3-deoxy-3-(4-methoxybenzamido)-β-D-galactopyranosyl) sulfane,
bis-(3-deoxy-3-(3-nitrobenzamido)-β-D-galactopyranosyl) sulfane, bis-(3-deoxy-3-[4-(dimethylamino)-benzamido]-β-D-galactopyranosyl) sulfane,
bis-(3-deoxy-3-(4-methylbenzamido)-β-D-galactopyranosyl) sulfane,
bis-(3-deoxy-3-(4-chlorobenzamido)-β-D-galactopyranosyl) sulfane,
bis-(3-deoxy-3-(4-tert-butylbenzamido)-β-D-galactopyranosyl) sulfane,
bis-(3-deoxy-3-(4-acetylbenzamido)-β-D-galactopyranosyl) sulfane,
-bis-(3-deoxy-3-[2-(3-carboxy)-naphthamido]-β-D-galactopyranosyl) sulfane,
bis-[3-deoxy-3-(3,4-methylenedioxy)benzamido]-β-D-galactopyranosyl) sulfane,
bis-(3-deoxy-3-(4-methoxycarbonylbenzamido)-β-D-galactopyranosyl) sulfane,
bis-(3-deoxy-3-(3-carboxybenzamido)-β-D-galactopyranosyl) sulfane,
bis-(3-deoxy-3-(3-benzyloxy-5-hydroxy-benzamido)-β-D-galactopyranosyl) sulfane,
bis-(3-deoxy-3-(3,5-dibenzyloxybenzamido)-β-D-galactopyranosyl) sulfane,
bis-(3-deoxy-3-(3-benzyloxy-5-methoxy-benzamido)-β-D-galactopyranosyl) sulfane,
bis-(3-deoxy-3-(3-benzyloxy-5-nonyloxy-benzamido)-β-D-galactopyranosyl) sulfane,
bis-(3-deoxy-3-(3-hydroxy-5-methoxy-benzamido)-β-D-galactopyranosyl) sulfane,
bis-(3-deoxy-3-(3-hydroxy-5-nonyloxy-benzamido)-β-D-galactopyranosyl) sulfane,
bis-(3-deoxy-3-[3-benzyloxy-5-(4-fluoro-benzyloxy)-benzamido]-β-D-galactopyranosyl) sulfane,
bis-(3-deoxy-3-[3-methoxy-5-(4-methyl-benzyloxy)-benzamido]-β-D-galactopyranosyl) sulfane, or
bis-(3-deoxy-3-(3-allyloxy-5-benzyloxy-benzamido)-β-D-galactopyranosyl) sulfane.

In one aspect, the present invention relates to the use of a compound according to the above-mentioned formula for the manufacture of a medicament for the treatment of any disorder relating to the binding of a galectin to receptors in a mammal. In one aspect of the invention, said galectin is galectin-3.

In another aspect, the invention relates to the use of a compound according to the above-mentioned formula for the manufacture of a medicament for the treatment of a disorder being selected from the group consisting of inflammation, septic shock, cancer, and autoimmune diseases such as reumatoid arthritis and multiple sclerosis. Preferably, said compound is for the manufacture of a medicament for the treatment of cancer.

In yet another aspect, the present invention relates to a pharmaceutical composition comprising a compound according to the above-mentioned formula as active ingredient together with a pharmaceutically acceptable adjuvant, diluent, excepient or carrier. A pharmaceutical composition of the invention comprises from 1 to 99 weight % of a pharmaceutically acceptable adjuvant, diluent, excepient or carrier and from 1 to 99 weight % of a compound according to above mentioned formula.

In one aspect, the invention relates to a method for inhibiting conditions associated with the binding of galectin to receptors in a mammal which method comprises administering to said mammal, an effective amount of a compound according to the above-mentioned formula. In one particularly important aspect of the invention, said galectin is galectin-3.

In another aspect, the invention relates to a method for inhibiting conditions associated with the binding of galectin to receptors in a mammal, which method comprises administering to said mammal an effective amount of a pharmaceutical composition according to the above. In one particularly important aspect of the invention, said galectin is galectin-3.

The pharmaceutical composition according to the present invention comprising a compound of the invention may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition of the present invention may be in the form of, for example, tablets, capsules, powders, solutions, transdermal patches or suppositories.

The pharmaceutical composition of the present invention may optionally comprise two or more compounds of the present invention. The composition may also be used together with other medicaments within the art for the treatment of related disorders.

The typical dosages of the compounds of the present invention vary within a wide range and depend on many factors, such as the route of administration, the requirement of the individual in need of treatment, the individual's body weight, age and general condition.

The adjuvants, diluents, excepients and/or carriers that may be used in the composition of the invention must be pharmaceutically acceptable in the sense of being compatible with the compounds and the other ingredients of the pharmaceutical composition, and not deleterious to the recipient thereof. The adjuvants, diluents, excepients and carriers that may be used in the pharmaceutical composition of the invention are well known to a person within the art.

Synthesis of Thiodigalactosides

The synthesis of the novel thiodigalactoside inhibitors followed methods well known to one skilled in the art (Scheme 1). The known compound 1,2,4,6-tri-O-acetyl-3-azido-3-deoxy-D-galactopyranose 1 (Lowary and Hindsgaul, 1994) was reduced to the corresponding amine with hydrogen gas over 10% palladium on charcoal, followed by immediate acylation with carboxylic acid chlorides to give the aromatic amides 2-6. The amides 2-6 were converted by treatment with hydrogen bromide in glacial acetic acid into the glycosyl bromides 7-11, which were used directly in reaction with sodium sulfide to give the protected thiodigalactoside derivatives 12-16. The O-acetyl protecting groups were removed via transesterfication with methanolic sodium methoxide to afford the final thiodigalactosides 17-21.

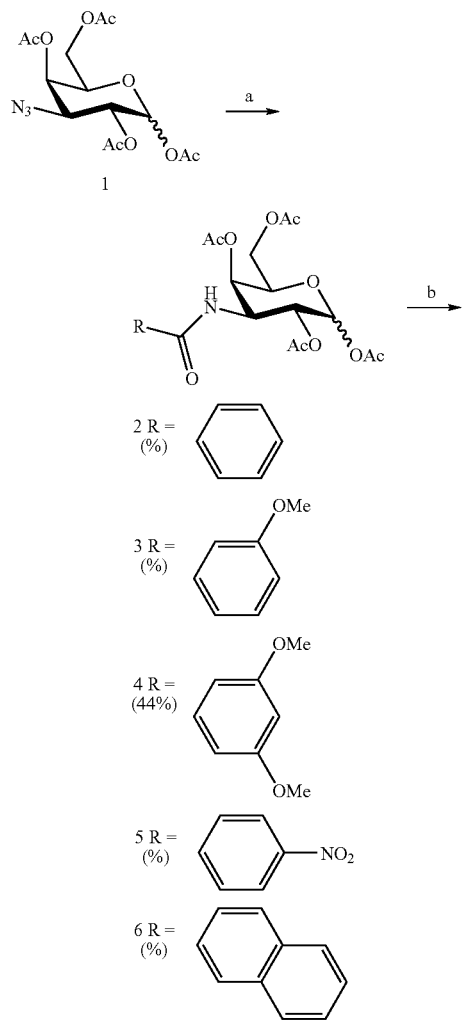

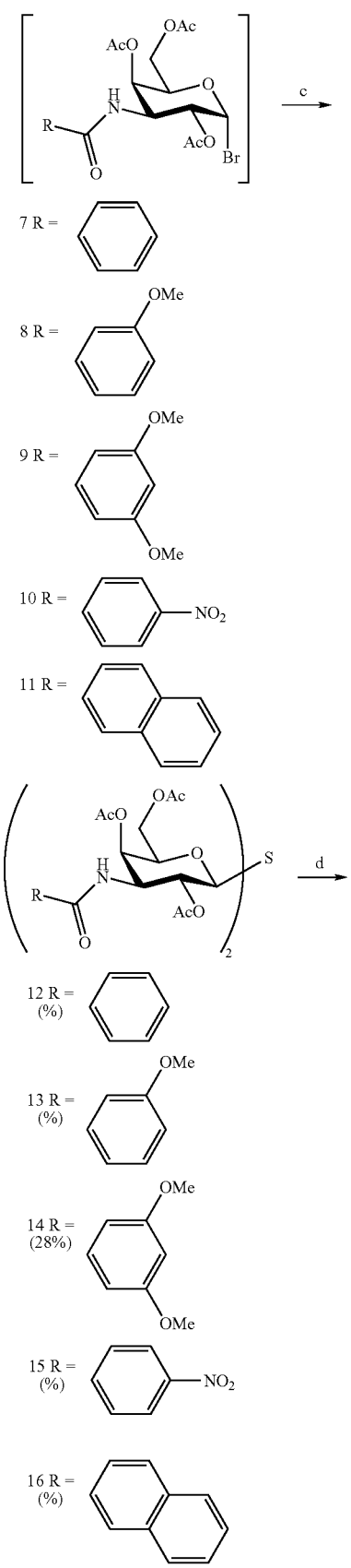

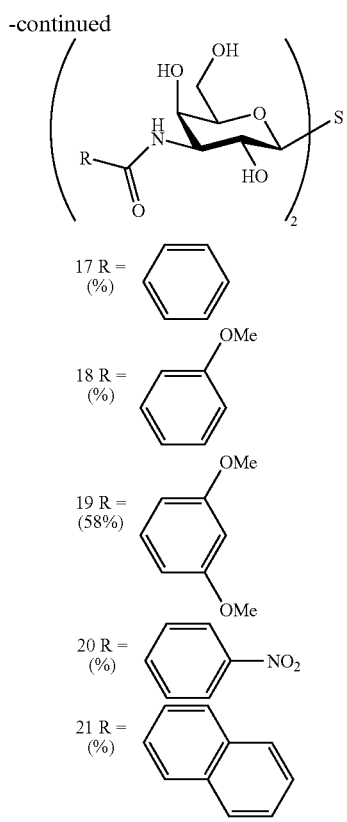

Scheme 1. a) $^{i}$H$_2$, EtOH, Pd/C 10%, HCl/Et$_2$O. $^{ii}$CH$_2$Cl$_2$, pyridine, carboxylic acid chloride. b) CH$_2$Cl$_2$, Ac$_2$O, 33% HBr in AcOH, c) Na$_2$S, MS4 Å, MeCN. d) NaOMe, MeOH.

Figure 4:
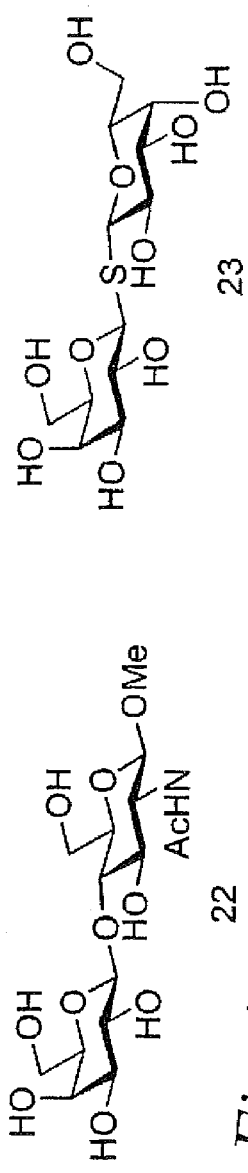
FIG. 4. Structures of known compounds used as reference galectin inhibitors; the methyl β-glycoside of N-acetyllactosamine 22 and thiodigalactoside 23.

Evaluation of new inhibitors 17-21 against galectin-3 Compounds 17-21 were evaluated for their efficiency in inhibiting galectin-3 in a known fluorescence polarization-based assay (Sörme et al., 2003a, 2004). (Table 1). The known inhibitors 22 and 23 of galectin-3 were included as reference compounds (FIG.4). All novel thiodigalactosides 17-21 were significantly better inhibitors of galectin-3 than the reference lactosamine 22 and unsubstituted parent thiodigalactoside 23. In particular, compounds 19-21 were unexpectedly powerful inhibitors with K$_d$ of 20-50 nM, which is more than three orders of magnitude improvement in comparison with the reference inhibitors 22 and 23 and unprecedented within the field of monovalent small-molecule inhibitors of galectins. The unexpectedly high inhibitor potency of 19-21 against galectin-3 renders them suitable to be active components in pharmaceutical compositions targeting conditions where galectin-3 plays a pathogenic role. Furthermore, the unnatural aromatic amido substituents are expected to improve hydrolytic stability and improve absorption in the gastrointestinal tract. The thioglycosidic linkage is also believed to improve stability towards hydrolysis and allow for more economical synthesis in comparison with synthesis of natural saccharide inhibitors of galectins.

TABLE 1

Affinity of compounds for galectin-3 as calculated from test by fluorescence polarization.

| | Structure | Tested Conc. (µM) | Calculated K$_d$ (nM) |
|---|---|---|---|
| 17 | 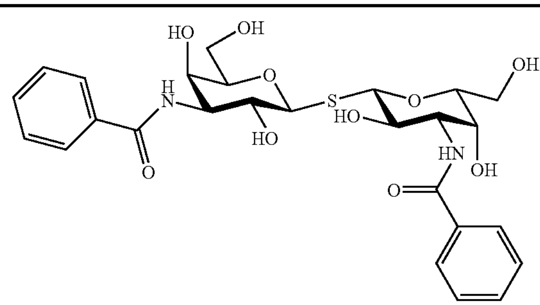 | 8 | 1440 |
| 18 | 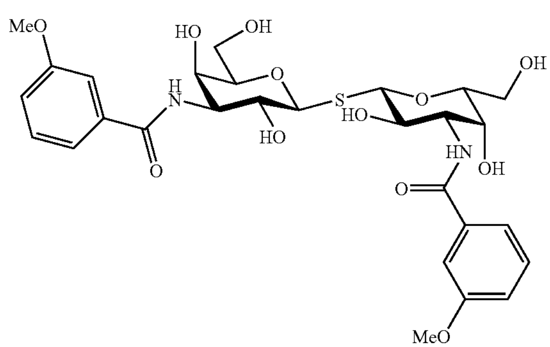 | 1.6 | 130 |

TABLE 1-continued

Affinity of compounds for galectin-3 as calculated from test by fluorescence polarization.

| | Structure | Tested Conc. (μM) | Calculated $K_d$ (nM) |
|---|---|---|---|
| 19 | [structure] | 1.6 | 20 |
| 20 | [structure] | 1.6 | 50 |
| 21 | [structure] | 1.6 | 30 |
| 22 | [structure] | 40 | 52000 |
| 23 | [structure] | 40 | 43000 |

METHODOLOGY/EXPERIMENTAL

General Synthetic Procedures

The compounds of this invention may be prepared by the following general methods and procedures. The galectin-3 assays of this invention may be performed by the following general methods and procedures. It should be appreciated that where typical or preferred process conditions (e.g. reaction temperatures, times, molar ratios of reactants, solvents, pressures, pH etc) are given, other process conditions may also be used unless otherwise stated. optimum reaction conditions may vary with the particular reactants, solvents used and pH etc., but such conditions can be determined by one skilled in the art by routine optimization procedures.

NMR-spectra were recorded with a Bruker DRX-400 instrument. Chemical shifts are given in ppm, with reference to internal residual solvent peaks. Chemical shifts and coupling constants were obtained from $^1$H-NMR and proton resonances were assigned from COSY experiments. High-resolution FAB mass spectra (HRMS) were recorded with a JEOL SX-120 instrument. Fluorescence polarization experiments were performed on a PolarStar instrument (BMG, Offenburg; Germany). Column chromatography was performed on $SiO_2$ (Matrex, 60 Å, 35-70 μm, Grace Amicon) and TLC was carried out on $SiO_2$ 60 $F_{254}$ (Merck) with detection under UV light and developed with aqueous sulfuric acid. Concentrations were made using rotary evaporation with bath temperature at or below 40° C. $CH_2Cl_2$ and $CH_3CN$ were dried by distillation from $CaH_2$. Microwell plates were from Costar, Corning, N.Y. (black polystyrene) Recombinant human galectin-3 was produced in *Escherichia coli* and purified as previously described (S. M. Massa et al, 1993). PBS was 118 mM NaCl, 67 mM Na/K-phosphate, pH 7.2, 2 mM EDTA, 4 mM β-mercaptoethanol.

Synthesis of Thiodigalactosides

Typical procedures for the synthesis of a 3,3'-bis-amido-thiodigalactoside derivative 1,2,4,6-Tetra-O-acetyl-3-deoxy-3-(3,5-dimethoxy-benzamido)-D-galactopyranose 4

1,2,4,6-Tetra-O-acetyl-3-azido-3-deoxy-D-galactopyranose 1 (167 mg, 0.45 mmol) was suspended in ethanol (5 ml), and palladium (10% on carbon, 17 mg) and HCl (1 ml of a 1M solution in diethyl ether) were added. The mixture was degassed and stirred at room temperature under a hydrogen atmosphere. After 1 h, dichloromethane was added, and the mixture was filtered through Celite and concentrated in vacuo. Half of the residue was dissolved in dichloromethane (2 ml) and pyridine (0.5 ml). 3,5-Dimethoxybenzoyl chloride (168 mg) was added, and the mixture was stirred at room temperature. After 18 h, TLC (1:1, heptane:ethyl acetate) showed the presence of a single carbohydrate product ($R_f$ 0.2). The reaction mixture was diluted with diethyl ether (30 ml) and washed with $H_2SO_4$ (30 ml of a 10% aqueous solution), $NaHCO_3$ (30 ml of a saturated aqueous solution), dried ($MgSO_4$), filtered and concentrated in vacuo. The residue was purified by flash column chromatography to give 1,2,4,6-tetra-O-acetyl-3-deoxy-3-(3,5-dimethoxybenzamido)-D-galactopyranose 4 (50 mg, 44%).

HRMS Calcd. for $C_{23}H_{29}NNaO_{12}$ (M+Na$^+$) 534.1587. Found 534.1576.

2,4,6-Tri-O-acetyl-3-deoxy-3-(3,5-dimethoxybenzamido)-α-D-galactopyranosyl bromide 9

1,2,4,6-Tetra-O-acetyl-3-deoxy-3-(3,5-dimethoxybenzamido)-D-galactopyranose 4 (50 mg, 0.098 mmol) was dissolved in dichloromethane (1 ml) which had been dried over 4 Å molecular sieves. Acetic anhydride (18 μl, 0.20 mmol) and HBr (0.2 ml, 33% in AcOH) were added, and the mixture was stirred under $N_2$ at room temperature. After 2 h 30 min, the reaction mixture was diluted with dichloromethane (30 ml) and poured into ice-water (30 ml). The organic phase was washed with $NaHCO_3$ (30 ml of a saturated aqueous solution), dried ($MgSO_4$), filtered and concentrated in vacuo to give 2,4,6-tri-O-acetyl-3-deoxy-3-(3,5-dimethoxybenzamido)-α-D-galactopyranosyl bromide 9, which was used without further purification.

Bis(2,4,6-tri-O-acetyl-3-deoxy-3-(3,5-dimethoxybenzamido)-β-D-galactopyranosyl) sulfane 14

Sodium sulfide nonahydrate (72 mg, 0.25 mmol) was dried in air using a heat gun and then allowed to cool under vacuum. Molecular sieves 4 Å (ca. 50 mg) were added. 2,4,6-Tri-O-acetyl-3-deoxy-3-(3,5-dimethoxybenzamido)-α-D-galactopyranosyl bromide 4, prepared above, was dissolved in distilled acetonitrile (1 ml) and added to the reaction vessel. The mixture was stirred at room temperature for 3 h. After this time, TLC (1:1, heptane:ethyl acetate) indicated the complete consumption of starting material ($R_f$ 0.3) and the presence of a major product ($R_f$ 0) as well as many minor components. The reaction mixture was diluted with ethyl acetate (30 ml) and poured into $H_2SO_4$ (30 ml of a 10% aqueous solution). The organic phase was dried ($MgSO_4$), filtered and concentrated in vacuo. The residue was purified by flash column chromatography (1:1 heptane:ethyl acetate→ethyl acetate) to give bis(2,4,6-tri-O-acetyl-3-deoxy-3-(3,5-dimethoxybenzamido)-β-D-galactopyranosyl) sulfane 14 (13 mg, 28%).

Bis-[3-deoxy-(3,5-dimethoxybenzamido)-β-D-galactopyranosyl]sulfane 19

Sodium (1.5 mg, 0.07 mmol) was dissolved in methanol (1 ml). Bis(2,4,6-tri-O-acetyl-3-deoxy-3-(3,5-dimethoxybenzamido)-β-D-galactopyranosyl) sulfane 14 (11 mg, 0.012 mmol) was dissolved in methanol (1 ml) and the sodium methoxide solution was added. The mixture was stirred at room temperature for 3 h. After this time, a precipitate had appeared. THF (3 ml) was added, and the precipitate dissolved. Duolite C436 (H$^+$) was added, and the mixture was stirred for 5 minutes. After this time, the mixture was filtered and concentrated in vacuo. The residue was purified by HPLC (gradient $H_2O$→MeCN) to give bis(3-deoxy-3-(3,5-dimethoxybenzamido)-β-D-galactopyranosyl) sulfane 19 (4.7 mg, 58%). White solid;

$^1$H NMR (400 MHz, D6-DMSO) δ 3.48-3.51 (6H, m, H-5, H-6, H-6') 3.69 (2H, atd, J 10.0 Hz, $J_{OH,2}$ 6.3 Hz, H-2), 3.79 (12H, s, 2×OCH$_3$), 3.85 (2H, d, $J_{3,4}$ 2.9 Hz, $J_{OH,4}$ 5.5 Hz, H-4), 3.94 (2H, ddd, $J_{2,3}$ 10.4 Hz, $J_{NH,3}$ 7.9 Hz, H-3), 4.60 (2H, at, J 5.6 Hz, OH-6), 4.72 (2H, d, $J_{1,2}$ 9.6 Hz, H-1), 4.87 (2H, d, OH-4), 4.93 (2H, d, OH-2), 6.63 (2H, t, J 2.2 Hz, Ar—H), 7.07 (2H, d, Ar—H), 8.07 (2H, d, NH); HRMS Calcd. for $C_{30}H_{40}O_{14}N_2SNa$ (M+Na$^+$) 707.2098. Found 707.2095.

In a similar manner were prepared from 1:

Bis-(3-deoxy-3-benzamido-β-D-galactopyranosyl) sulfane 17

White oil;
$^1$H NMR (400 MHz, CD$_3$OD) δ 3.67-3.74 (4H, m, H-5, H-6), 3.80 (2H, dd, $J_{5,6'}$ 6.6 Hz, $J_{6,6'}$ 10.5 Hz, H-6'), 3.89 (2H, at, J 10.0 Hz, H-2), 4.03 (2H, d, $J_{3,4}$ 2.9 Hz, H-4), 4.17 (2H, dd, $J_{2,3}$ 10.3 Hz, H-3), 4.83 (2H, d, $J_{1,2}$ 9.7 Hz, H-1), 7.47 (4H, at, J 7.4 Hz, Ar—H), 7.54 (2H, at, J 7.4 Hz, Ar—H), 7.88 (4H, at, J 7.1 Hz, Ar—H); $□_c$ (100.6 MHz, CD$_3$OD) 58.8 (d, C-3), 62.9 (t, C-6), 69.2, 69.4 (2×d, C-2, C-4), 81.7 (d, C-5), 86.4 (d, C-1), 128.6, 129.5, 132.7 (3×d, Ar—CH), 135.9 (s, Ar—C), 170.6 (s, C=O); HRMS Calcd. for $C_{26}H_{32}O_{10}N_2SNa$ (M+Na$^+$) 587.1675. Found 587.1676.

Bis-[3-deoxy-3-(3-methoxybenzamido)-β-D-galactopyranosyl]sulfane 18

White solid;
$^1$H NMR (400 MHz, D6-DMSO) δ 3.46-3.63 (12H, br m, OH-2, OH-4, OH-6, H-5, H-6, H-6'), 3.70 (2H, at, J 10.0 Hz, H-2), 3.81 (6H, s, OCH$_3$), 3.86 (2H, d, J$_{3,4}$ 2.9 Hz, H-4), 3.95 (2H, m, H-3), 4.72 (2H, d, J$_{1,2}$ 9.7 Hz, H-1), 7.08 (2H, dd, J 2.2 Hz, J 8.1 Hz, Ar—H), 7.37 (2H, at, J 7.9 Hz, Ar—H), 7.46 (2H, d, J 2.2 Hz, Ar—H), 7.48 (2H, d, J 7.8 Hz, Ar—H), 8.07 (2H, d, J$_{NH,3}$ 7.9 Hz, NH); HRMS Calcd. for C$_{28}$H$_{36}$O$_{12}$N$_2$SNa (M+Na$^+$) 647.1887. Found 647.1888.

Bis-[3-deoxy-3-(4-nitrobenzamido)-β-D-galactopyranosyl]sulfane 20

White solid;
$^1$H NMR (400 MHz, D6-DMSO) δ 3.51-3.52 (6H, m, H-5, H-6, H-6'), 3.72 (2H, atd, J 10.0 Hz, J$_{OH,2}$ 6.1 Hz, H-2), 3.89 (2H, m, H-4), 3.97 (2H, ddd, J$_{2,3}$ 10.5 Hz, J$_{3,4}$ 3.0 Hz, J$_{NH,3}$ 7.9 Hz, H-3), 4.61 (2H, at, J 5.5 Hz, OH-6), 4.73 (2H, d, J$_{1,2}$ 9.8 Hz, H-1), 4.96-4.98 (4H, m, OH-2, OH-4), 8.15, 8.32 (8H, 2xd, J 8.9 Hz, Ar—H), 8.56 (2H, d, NH); HRMS Calcd. for C$_{26}$H$_{30}$O$_{14}$N$_4$SNa (M+Na$^+$) 677.1377. Found: 677.1367.

Bis-[3-deoxy-3-(2-naphthamido)-β-D-galactopyranosyl]sulfane 21

White solid;
$^1$H NMR (400 MHz, CDCl$_3$:CD$_3$OD, 1:1) δ 3.67-3.76 (4H, m, H-5, H-6), 3.83 (2H, dd, J$_{5,6'}$ 6.8 Hz, J$_{6,6'}$ 11.2 Hz, H-6'), 3.93 (2H, at, J 10.0 Hz, H-2), 4.08 (2H, d, J$_{3,4}$ 3.0 Hz, H-4), 4.22 (2H, dd, J$_{2,3}$ 10.3 Hz, H-3), 4.78 (2H, d, J$_{1,2}$ 9.7 Hz, H-1), 7.51-7.56 (4H, m, Ar—H), 7.86-7.95 (8H, m, Ar—H), 8.41 (2H, s, Ar—H); HRMS Calcd. for C$_{34}$H$_{36}$O$_{10}$N$_2$SNa (M+Na$^+$) 687.1988. Found 687.1987.

Evaluation of 17-23 as Inhibitors of Galectin-3 by use of Fluorescense Polarization Compounds 17-21 were evaluated for their efficiency in inhibiting galectin-3 in a known fluorescence polarization-based assay (Sörme et al., 2003a, 2004). To 100 µL of galectin-3 (1 µM) and a fluorescent probe (2-(fluorescein-5/6-ylcarbonyl)-aminoethyl 4-O-[3-O-(4-methoxybenzyl)-β-D-galactopyranosyl]-β-D-glucopyranoside, 0.1 µM) were added inhibitor solution (3.2-80 µM, 100 µL), the plate was incubated under slow rotary shaking in the dark for 5 minutes, and fluorescence polarization measured at room temperature. The fluorescence was measured from above in 96 well microtiter plates (black polystyrene, Costar, Corning, N.Y.) using a PolarStar instrument (BMG, Offenburg; Germany). Control wells containing only fluorescent probe or fluorescein were included. All dilutions and measurements were done in PBS.

Examples of in vivo Efficacy of Galectin Inhibition in Inflammation and Cancer

Inflammation

As mentioned above, many studies suggest a role for galectin-3 in enhancement of the inflammatory response. For example, the addition of galectin-3 to neutrophil leukocytes from an inflammatory site, or primed by exposure to LPS, results in increased generation of toxic oxygen radicals. Lactose can inhibit this response (Karlsson et al., 1998; Almquist et al., 2001). In another study (Sano et al., 2000), galectin-3 was found to be chemotactic to macrophages and monocytes, both in vitro and in vivo. Either lactose or the isolated-CRD of galectin-3 (galectin 3C), able to bind the same saccharide receptor as galectin-3 but not cross link it (see below), acted as inhibitors of this response. The substances described in the present invention would be much more effective as inhibitors of the above mentioned responses than lactose because they are much more potent galectin-3 inhibitors. They would also be much more useful in vivo than lactose and the galectin-3C because they are small molecules, more hydrophobic and probably more stable to degradation.

Cancer

As mentioned above, several studies of models of human cancer in mice indicate that enhanced expression of galectin-3 results in faster tumor growth and more metastasis (Bresalier et al., 1998; reviewed by Leffler, 2001 and Takenaka et al in Leffler (editor), 2004b). Injection of a saccharide with inhibitory potency to galectin-3, but perhaps also other proteins, was reported to diminish prostate cancer in rat (Pienta et al., 1995). Hence, potent small-molecule inhibitors of galectin-3 are expected to have similar anticancer effects as galectin-3C (John et al., 2003).

REFERENCES

Ahmad, N., Gabius, H. J., Andre, S., Kaltner, H., Sabesan, S., Roy, R., Liu, B., Macaluso, F., and Brewer, C. F. (2004) Galectin-3 precipitates as a pentamer with synthetic multivalent carbohydrates and forms heterogeneous cross-linked complexes. *J. Biol. Chem.* 279: 10841-10847.

Almkvist, J., Fäldt, J., Dahlgren, C., Leffler, H., and Karlsson, A. (2001) Lipopolysaccharide-induced gelatinase granule mobilization primes neutrophils for activation by galectin-3 and f-Met-Leu-Phe. *Infect. Immun.* Vol. 69: 832-837.

André, S., Ortega, P. J. C., Perez, M. A., Roy, R., and Gabius, H.-J.(1999) Lactose-containing starburst dendrimers: influence of dendrimer generation and binding-site orientation of receptors (plant/animal lectins and immunoglobulins) on binding properties. *Glycobiology* 11:1253-1262.

André, S., Kaltner, H., Furuike, T., Nishimura, S.-I., and Gabius, H.-J. (2004) Persubstituted Cyclodextrin-Based Glycoclusters as Inhibitors of Protein-Carbohydrate Recognition Using Purified Plant and Mammalian Lectins and Wild-Type and Lectin-Gene-Transfected Tumor Cells as Targets. *Bioconj. Chem.* 15:87-98.

Arnusch, C. J., André, S., Valentini, P., Lensch, M., Russwurm, R., Siebert, H.-C., Fischer, M. J. E., Gabius, H.-J., and Pieters, R. J. (2004) Interference of the galactose-dependent binding of lectins by novel pentapeptide ligands. *Bioorg. Med. Chem. Lett.* 14:1437-1440.

Barondes, S. H., Cooper, D. N. W., Gitt, M. A., and Leffler, H. (1994). Galectins. Structure and function of a large family of animal lectins. *J. Biol. Chem.* 269:20807-20810.

Bresalier, R. S., Mazurek, N., Sternberg, L. R., Byrd, J. C., Yunker, C. K., Nangia-Makker, P., Raz, A. (1998) Metastasis of human colon cancer is altered by modifying expression of the beta-galactoside-binding protein galectin 3. *Gastroenterology* 115:287-296.

Brewer, C. F., Miceli, M. C., and Baum, L. G. (2002) Clusters, bundles, arrays and lattices: novel mechanisms for lectin-saccharide-mediated cellular interactions. *Curr. Opin. Struct. Biol.* 12: 616-623.

David, A., Kopecková, P., Minko, T., Rubinstein, A., and Kopecek, J. (2004) Design of a multivalent galactoside ligand for selective targeting of HPMA copolymer-doxorubicin conjugates to human colon cancer cells. *Eur. J. Cancer* 40: 148-157.

Glinsky, G. V., Price, J. E., Glinsky, V. V., Mossine, V. V., Kiriakova, G., Metcalf, J. B. (1996) Inhibition of human breast cancer metastasis in nude mice by synthetic glycoamines. *Cancer Res.* 56:5319-5324.

Houzelstein, D., Goncalves, I. R., Fadden, A. J., Sidhu, S. S., Cooper, D. N., Drickamer, K., Leffler, H., and Poirier, F. (2004) Phylogenetic Analysis of the Vertebrate Galectin Family. *Mol. Biol. Evol.* ????.

Huflejt M E, Mossine V V, Naidenko O, Jazayeri M, Rogers P, Tinari N, Iacobelli S, Elliot, M., Lustgarten J and Croft, M. (2001) Synthetic lactulose amines bind tumor-promoting galectins-1 and -4, and inhibit breast cancers in Her-2/neu transgenic mice., 24th Annual San Antonio Breast Cancer Symposium, abstract.

Huflejt, M. E. and Leffler, H. (2004) Galectin-4 in normal tissues and cancer. *Glycoconj. J.* 20: in press.

John, C. M., Leffler, H., Kahl-Knutsson, B., Svensson, I., and Jarvis, G. A. (2003) Truncated Galectin-3 Inhibits Tumor Growth and Metastasis in Orthotopic Nude Mouse Model of Human Breast *Cancer. Clin. Cancer Res.* 9:2374-2383.

Karima, R., Matsumoto, S., Higahsi, H., Matsushima, K. (1999) The molecular pathogenesis of Endotoxic Shock and Organ Failure. *Molecular Medicine Today* 5:123-132.

Karlsson, A., Follin, P, Leffler, H., Dahlgren, C. (1998) Galectin-3 activates the NADPH-oxidase in exudated but not peripheral blood neutrophils. *Blood* 91:3430-3438.

Leffler, H. and Barondes, S. H. (1986) Specificity of binding of three soluble rat lung lectins to substituted and unsubstituted mammalian beta-galactosides. *J. Biol. Chem.* 261: 10119-10126.

Leffler, H. Galectins Structure and Function—A Synopsis in Mammalian Carbohydrate Recognition Systems (Crocker, P. ed.) Springer Verlag, Heidelberg, 2001 pp. 57-83.

Leffler, H., Carlsson, S., Hedlund, M., Qian, Y. and Poirier, F. (2004) Introduction to galectins. *Glycoconj. J.* 19: 433-440.

Leffler, H., editor, (2004b) Special Issue on Galectins. *Glycoconj. J.* 19: 433-638.

Lobsanov, Y. D. and Rini, J. M. (1997) Galectin Structure. *Trends. Glycosci. Glycotech.* 45:145-154.

Lowary, T. L. and Hindsgaul, O. (1994) Recognition of synthetic O-methyl, epimeric, and amino analogues of the acceptor α-L-Fucp-(1-2)-β-D-Galp-OR by the blood-group A and B gene-specified glycosyltransferases. *Carbohydr. Res.* 251:33-67.

Massa, S. M., Cooper, D. N. W., Leffler, H., Barondes, S. H. (1993) L-29, an endogenous lectin, binds to glycoconjugate ligands with positive cooperativity. *Biochemistry* 32; 260-267.

Naidenko, O., Kronenberg, M., Glinsky, G., and Huflejt, M.E. (2000) Interaction of galectins with low molecular weight lactosylaminoconjugates. *Glycobiology* 10: abstract 60.

Nangia-Makker, P., Hogan, V., Honjo, Y., Baccarini, S., Tait, L., Bresalier, R., and Raz, A. (2002) Inhibition of human cancer cell growth and metastasis in nude mice by oral intake of modified citrus pectin, *J. Natl. Cancer Inst.* 94:1854-1862.

Pienta, K. J., Naik, H., Akhtar, A., Yamazaki, K., Replogle, T. S., Lehr, J., Donat, T. L., Tait, L., Hogan, V., Raz, A. (1995) Inhibition of spontaneous metastasis in a rat prostate cancer model by oral administration of modified citrus pectin. *J. Natl. Cancer Inst.* 87:348-353

Platt, D. and Raz, A. (1992) *J. Natl. Cancer. Inst.* 84: 438-442.

Pohl, N. L. and Kiessling, L. L. (1999) Scope of multivalent ligand function: Lactose-bearing neoglycopolymers by ring-opening metathesis polymerization. *Synthesis* 1515-1519.

Poirier, F. (2002) Roles of galectins in vivo. *Biochem. Soc. Symp.* 69: 95-103.

Rubinstein, N., Alvarez, M., Zwirner, N. W., Toscano, M. A., Ilarregui, J. M., Bravo, A., Mordoh, J., Fainboim, L., Podhajcer, O. L., and Rabinovich, G. A. (2004) Targeted inhibition of galectin-1 gene expression in tumor cells results in heightened T cell-mediated rejection; A potential mechanism of tumor-immune privilege. *Cancer Cell* 5: 241-251.

Sano, H., Hsu, D. K., Yu, L., Apgar, J. R., Kuwabara, I., Yamanaka, T., Hirashima, M., Liu, F. T. (2000) Human galectin-3 is a novel chemoattractant for monocytes and macrophages. *J. Immunol.* 165:2156-2164.

Seetharaman, J., Kanigsberg, A., Slaaby, R., Leffler, H., Barondes, S. H., Rini, J. M. (1998) X-ray crystal structure of the human galectin-3 carbohydrate recognition domain at 2.1-A resolution. *J. Biol. Chem.* 273:13047-13052.

Sörme, P., Qian, Y., Nyholm, P.-G., Leffler, H., Nilsson, U. J. (2002) Low micromolar inhibitors of galectin-3 based on 3'-derivatization of N-acetyllactosamine. *Chem. Bio. Chem* 3:183-189.

Sörme, P., Kahl-Knutsson, B., Wellmar, U., Nilsson, U. J., and Leffler H. (2003a) Fluorescence polarization to study galectin-ligand interactions. *Meth. Enzymol.* 362: 504-512.

Sörme, P., Kahl-Knutsson, B., Wellmar, U., magnusson, B.-G., Leffler H., and Nilsson), U. J. (2003b) Design and synthesis of galectin inhibitors. *Meth. Enzymol.* 363: 157-169.

Sörme, P., Kahl-Knutsson, B., Huflejt, M., Niusson, U. J., and Leffler H. (2004) Fluorescence polarization as an analytical tool to evaluate galectin-ligand interactions. *Anal. Biochem.* accepted for publication.

Trahey, M. and Weissman, I. L. (1999) Cyclophilin C-associated protein: a normal secreted glycoprotein that down-modulates endotoxin and proinflammatory responses in vivo. *Proc. Natl. Acad. Sci. USA* 96:3006-3011.

Vrasidas, I., André, S., Valentini, P., Böck, C., Lensch, M., Kaltner, H., Liskamp, R. M. J., Gabius, H.-J., and Pieters, R. J. (2003) Rigidified multivalent lactose molecules and their interactions with mammalian galectins: a route to selective inhibitors. *Org. Biomol. Chem.* 1: 803-810.

The invention claimed is:

1. A compound of the general formula (I):

wherein the configuration of one of the pyranose rings is β-D-galacto;

X is selected from the group consisting of O, S, SO, or $SO_2$,

Y is selected from the group consisting of O or NH;

Z is selected from the group consisting of O or NH;

$R^1$ and $R^3$ are independently selected from the group consisting of CO, SO, or $CH_2$;

$R^2$ and $R^4$ are independently selected from the group consisting of;

a) a phenyl group substituted with at least one carboxy group, a phenyl group substituted with at least one halogen, a phenyl group substituted with at least one alkoxy group having 1 to 12 carbon atoms, a phenyl group substituted with at least one nitro group, a phenyl group substituted with at least one sulfo group, a phenyl group substituted with at least one amino group, a phenyl group substituted with at least one alkylamino group having 1 to 12 carbon atoms, a phenyl group substituted with at least one arylamino group having 1 to 12 carbon atoms, a phenyl group substituted with at least one dialkylamino group, a phenyl group substituted with at least one hydroxy group, a phenyl group substituted with at least one carbonyl group and a phenyl group substituted with at least one substituted carbonyl group;

b) a naphthyl group, a naphthyl group substituted with at least one carboxy group, a naphthyl group substituted with at least one halogen, a naphthyl group substituted with at least one alkoxy group having 1 to 12 carbon atoms, a naphthyl group substituted with at least one nitro group, a naphthyl group substituted with at least one sulfo group, a naphthyl group substituted with at least one amino group, a naphthyl group substituted with at least one alkylamino group having 1 to 12 carbon atoms, a naphthyl group substituted with at least one arylamino group having 1 to 12 carbon atoms, a naphthyl group substituted with at least one dialkylamino group, a naphthyl group substituted with at least one hydroxy group, a naplithyl group substituted with at least one carbonyl group and a naphthyl group substituted with at least one substituted carbonyl group, and whereby the alkyl group being a straight- or branched-chain having 1 to 12 carbon atoms to form a cycle comprising from 3 to 12 carbon atoms;

c) a heteroaryl group, a heteroaryl group substituted with at least one carboxy group, a heteroaryl group substituted with at least one halogen, a heteroaryl group substituted with at least one alkoxy group, a heteroaryl group substituted with at least one nitro group, a heteroaryl group substituted with at least one sulfo group, a heteroaryl group substituted with at least one amino group, a heteroaryl group substituted with at least one alkylamino group, a heteroaryl group substituted with at least one dialkylamino group, a heteroaryl group substituted with at least one arylamino group, a heteroaryl group substituted with at least one hydroxy group, a heteroaryl group substituted with at least one carbonyl group and a heteroaryl group substituted with at least one substituted carbonyl group;

$R^6$ and $R^8$ are independently selected from the group consisting of a hydrogen, an acyl group being aliphatic or aromatic and having 2 to 7 carbon atoms, or a benzyl group;

$R^7$ is selected from the group consisting of a hydrogen, an acyl group being aliphatic or aromatic and having 2 to 7 carbon atoms, or a benzyl group; and $R^9$ is selected from the group consisting of a methyl group or a hydroxymethyl group.

2. A compound according to claim 1 wherein Y=NH.

3. A compound according to claim 1 wherein Z=NH.

4. A compound according to claim 1 wherein X=S.

5. A compound according to claim 1, wherein $R^1$ is CO.

6. A compound according to claim 1, wherein $R^3$ CO.

7. A compound according to claim 1, wherein $R^2$ is selected from the group consisting of a phenyl group substituted with at least one carboxy group, a phenyl group substituted with at least one halogen, a phenyl group substituted with at least one alkoxy group having 1 to 12 carbon atoms, a phenyl group substituted with at least one nitro group, a phenyl group substituted with at least one sulfo group, a phenyl group substituted with at least one amino group, a phenyl group substituted with at least one alkylamino group having 1 to 12 carbon atoms, a phenyl group substituted with at least one arylamino group having 1 to 12 carbon atoms, a phenyl group substituted with at least one dialkylamnino group, a phenyl group substituted with at least one hydroxy group, a phenyl group substituted with at least one carbonyl group and a phenyl group substituted with at least one substituted carbonyl group.

8. A compound according to claim 1, wherein $R^4$ is selected from the group consisting of a phenyl group substituted with at least one carboxy group, a phenyl group substituted with at least one halogen, a phenyl group substituted with at least one alkoxy group having 1 to 12 carbon atoms, a phenyl group substituted with at least one nitro group, a phenyl group substituted with at least one sulfo group, a phenyl group substituted with at least one amino group, a phenyl group substituted with at least one alkylamino group having 1 to 12 carbon atoms, a phenyl group substituted with at least one arylamino group having 1 to 12 carbon atoms, a phenyl group substituted with at least one dialkylamnino group, a phenyl group substituted with at least one hydroxy group, a phenyl group substituted with at least one carbonyl group and a phenyl group substituted with at least one substituted carbonyl group.

9. A compound according to claim 1, wherein $R^6$, $R^7$, and $R^8$ are hydrogen.

10. A compound according to claim 1, wherein $R^9$ is a hydroxymethyl group.

11. A compound according to claim 1, wherein the carbon attached to $R^8$ has stereoconfiguration R.

12. A compound according to claim 1, wherein said compound is bis-(3-deoxy-3-benzamido-β-D-galactopyranosyl)sulfane (17), bis-(3-deoxy-3-(3-methoxybenzamido)-β-D-galactopyranosyl)sulfane (18), bis-(3-deoxy-(3,5-dimethoxybenzamido)-β-D-galactopyranosyl)sulfane (19), bis-(3-deoxy-3-(4-nitrobenzamido)-β-D-galactopyranosyl)sulfane (20), bis(3-deoxy-3-(2-naphthamido)-β-D-galactopyranosyl) sulfane (21).

13. A compound according to claim 1, for use as a medicament.

14. A pharmaceutical composition comprising a compound according to claim 1 as active ingredient together with a pharmaceutically acceptable adjuvant, diluent, excepient or carrier.

15. A pharmaceutical composition according to claim 14, comprising from 1 to 99 weight % of a pharmaceutically acceptable adjuvant, diluent, excepient or carrier and from 1 to 99 weight % of a compound according to claim 1.

* * * * *